United States Patent [19]

Ramwell et al.

[11] Patent Number: 5,002,965

[45] Date of Patent: Mar. 26, 1991

[54] USE OF GINKGOLIDES TO PREVENT REPERFUSION INJURY IN ORGAN TRANSPLANTATION

[75] Inventors: Peter W. Ramwell; Marie L. Foegh, both of McLean, Va.

[73] Assignee: Societe de Conseils de Recherches et d'Applications Scientifiques (S.C.R.A.S.), France

[21] Appl. No.: 349,035

[22] Filed: May 9, 1989

[51] Int. Cl.$^5$ ............................................. A61K 31/34
[52] U.S. Cl. .................................. 514/468; 549/297; 424/195.1; 435/1
[58] Field of Search .................... 514/468; 549/297; 424/195.1; 435/1

[56] References Cited

U.S. PATENT DOCUMENTS

| | | | |
|---|---|---|---|
| 4,008,754 | 2/1977 | Kraushaar et al. | 165/2 |
| 4,242,883 | 1/1981 | Toledo-Pereyra | 62/306 |
| 4,473,637 | 9/1984 | Guibert | 435/1 |
| 4,681,839 | 7/1987 | Swartz | 435/1 |
| 4,734,280 | 3/1988 | Braquet | 424/195.1 |
| 4,797,277 | 1/1989 | Arfors | 424/85.8 |
| 4,798,824 | 1/1989 | Belzer et al. | 435/1 X |

FOREIGN PATENT DOCUMENTS 3710921 7/1988 Fed. Rep. of Germany .

OTHER PUBLICATIONS

Foegh et al., "PAF and BN 52021 in Organ Transplant Rejection", Ginkgolides–Chemistry, Biology, Pharmacology and Clinical Perspectives, vol. 1, edited by P. Braquet, J. R. Prous Science Publishers, pp. 743–748 (May 1, 1988).
Muino et al., Chemical Abstracts, 108, 179781d (1988).
Nakanishi, "The Ginkgolides", Pure and Applied Chemistry, 14, pp. 89–113 (1983).
Okabe et al., "Ginkgolides", J. Chem. Soc. (c), pp. 2201–2206 (1967).
Foegh et al., Transplantation, 1986, vol. 42, No. 1, pp. 86–88.
Khirabadi et al., Transplantation, 1987, vol. 43, No. 5, pp. 626–630.

*Primary Examiner*—John W. Rollins
*Attorney, Agent, or Firm*—Birch, Stewart, Kolasch & Birch

[57] ABSTRACT

A living tissue or living cell preservation solution comprising an effective amount of a ginkgolide to reduce reperfusion injury in living tissue which has been stored therein and a substance or mixture or substances present in an amount sufficient to produce an osmotic pressure in said solution approximately equal to the osmotic pressure or mammalian cell and a method for preventing or reducing reperfusion injury in transplanted mammalian organs, which comprises contacting an organ prior to reperfusion with an effective amount of a ginkgolide to reduce reperfusion injury in said organ.

15 Claims, 1 Drawing Sheet

USE OF GINKGOLIDES TO PREVENT REPERFUSION INJURY IN ORGAN TRANSPLANTATION

BACKGROUND OF THE INVENTION

Lung transplantation has been an effective treatment for patients with end stage pulmonary disease. The major challenge facing lung transplantation is organ availability. In efforts to increase organ availability research has focused on improving organ preservation. The current standard is hypothermic storage with solutions that approximate an intracellular electrolyte composition (hyperkalemic, hypermagnesemic) and substrate enhancement (dextrose+/−insulin).

One problem encountered during organ transplantation is reperfusion injury to the transplanted organ after it has been transplanted to the organ recipient. Attempts have been made in the past to minimize reperfusion injury, however, the discovery of a more effective means for minimizing reperfusion injury is needed. Recent attention has been focused on limiting reperfusion injury by blocking the generation of or scavenging oxygen derived free oxygen radicals. One such approach has been to include allopurinol in the reperfusion solution. Various patents describe solutions for the preservation of organs. Examples of such patents are U.S. Pat. Nos. 4,798,824 to Belzer et al and 4,797,277 to Arfors.

In spite of all these approaches, preservation of organs such as lungs, pancreas, heart and liver is still a problem. For example, in lung preservation the current preservation time is so short that the donor has to be next to the recipient. In other words there is no preservation time.

SUMMARY OF THE INVENTION

It is an object of the present invention to provide a method for preventing or reducing reperfusion injury in transplanted mammalian organs which comprises contacting an organ to be transplanted or prior to reperfusion contacting an organ which has been transplanted with an effective amount of a ginkgolide to reduce reperfusion injury in the organ. Ideally, the ginkgolide should be present in the organ tissue after it has been transplanted. This can be accomplished either by placing the organ to be transplanted in an organ preservation solution containing a ginkgolide during the transplant procedure, by administering the ginkgolide to the organ recipient and/or by administering the ginkgolide to the organ donor.

When the ginkgolide is administered to the organ donor, it can be administered in any manner which allows the ginkgolide to reach the organ prior to removal of the organ from the donor. For example, the ginkgolide may be administered to the organ donor intravenously, intraperitoneally, intramuscularly or orally, however, intravenous administration is preferred. The ginkgolide may be administered to the organ donor about 10 minutes to 12 hours prior to removal of the organ from the donor, preferably 10 minutes to 2 hours prior to removal of the organ from the organ donor. The ginkgolide may be administered in an amount of 1 to 20 mg/kg of body weight of the donor, preferably 2 to 10 mg/kg of body weight of the donor, most preferably about 5 mg/kg of body weight of the donor.

As mentioned previously, the ginkgolide may also be added to the organ preservation solution to help prevent reperfusion injury after the organ is transplanted to the organ recipient. The ginkgolide may be present in the organ preservation solution in an amount of 50 to 600 mg/l, preferably 100 to 400 mg/l, most preferably 250-300 mg/l.

The ginkgolide is also desirably administered to the organ recipient. The ginkgolide may be administered to the organ recipient intravenously, intramuscularly or orally, preferably intravenously. The ginkgolide should be administered to the organ recipient prior to reperfusion of the transplanted organ within the recipient. The ginkgolide is preferably administered to the organ recipient approximately 1 to 30 minutes prior to reperfusion, preferably just prior to reperfusion of the organ. The ginkgolide may be administered in an amount of 1 to 20 mg/kg body weight of the organ recipient, preferably 2 to 10 mg/kg body weight of the organ recipient, most preferably 5 mg/kg body weight of the organ recipient.

The method of the present invention can be utilized for various types of warm-blooded mammals. This procedure has been tested on dogs, however, this procedure may be used on various types of warm-blooded mammals such as cats, guinea pigs, rats, mice and monkeys. However, it is contemplated that the present invention will also be useful in transplanting human or non-human organs or living tissue into a human being.

The procedure of the present invention has been tested with lungs, however, it is contemplated that the method of the present invention may also be useful in the transplantation of other types of organs such as transplantation of hearts, kidneys, livers, etc.

DETAILED DESCRIPTION OF THE INVENTION

Figure 1:
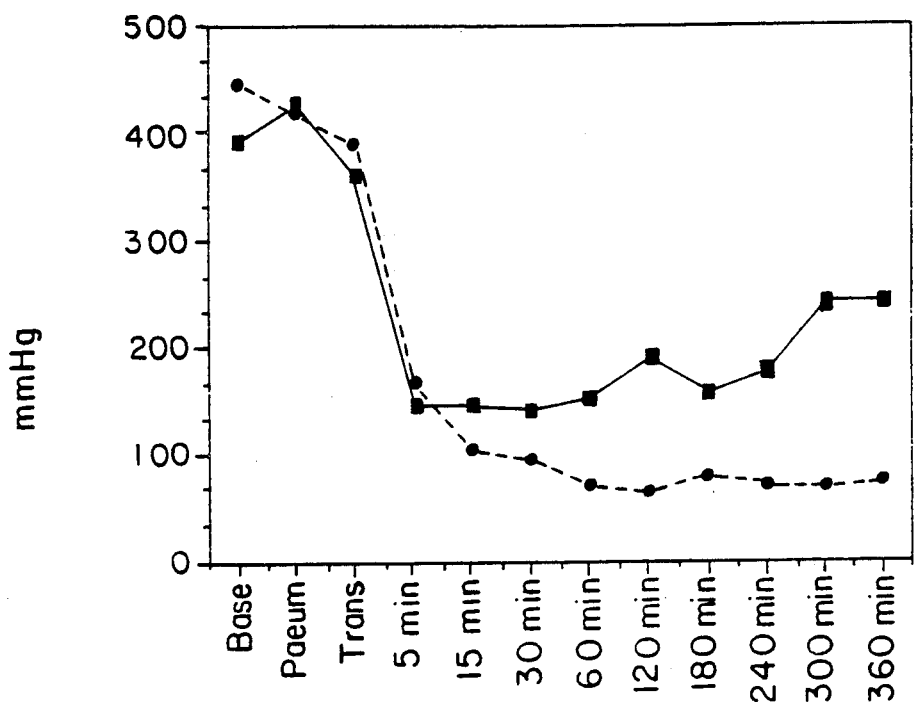
FIG. 1 is a graph showing the results of the blood gas analysis study described in Example 1 wherein the solid line represents the present invention and the dotted line represents a control.

The term "ginkgolide" as used herein includes all of the naturally occurring ginkgolides which are derived from the gymnospermous tree *Ginkgo biloba* as well as synthetically produced ginkgolides and pharmacologically active derivatives and salts thereof and mixtures thereof. Commonly available ginkgolides include Ginkgolides A, B, C, J and M. Ginkgolides are twenty carbon cage molecules, incorporating a t-butyl group and six 5-membered rings A to F including a spiro [4.4] nonane, a tetrahydrofuran cycle and three lactone rings. The various ginkgolide structures differ only by the number and position of hydroxyl groups on the $C_1$, $C_3$ or $C_7$ of the spirononane framework. These compounds have been named Ginkgolides A, B, C, J and M as follows:

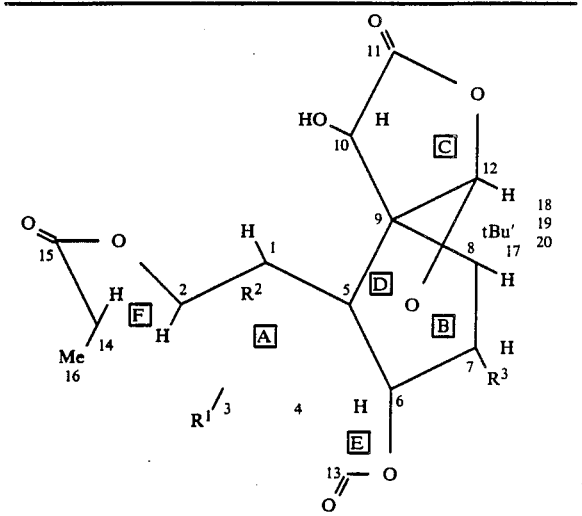

| Ginkgolide | R₁ | R₂ | R₃ |
|---|---|---|---|
| A | OH | H | H |
| B | OH | OH | H |
| C | OH | OH | OH |
| J | OH | H | OH |
| M | H | OH | OH |
| synthetic | OH | OMe | H |
| synthetic | OH | OEt | H |

Ginkgolides A, B, C, J, M and the 1-methoxy and 1-ethoxy derivatives of ginkgolide B.

Ginkgolides A, B, C and M represent the four PAF (platelet activating factor) antagonists initially characterized in the prior art. Another ginkgolide, ("J"), has also been identified in leaves of *Ginkgo biloba*. In addition, ginkgolides with various substitutions have been prepared from the natural products for pharmacological investigation, for example, the 2,3-dehydro, 1-methoxy, and 1-ethoxy derivatives of Ginkgolide B. Ginkgolide B may be prepared synthetically as reported by Corey et al, Total Synthesis of (+)-Ginkgolide B, Journal of the American Chemical Society, 110, 649–651 (1988).

Ginkgolide A, Ginkgolide B, Ginkgolide C, and Ginkgolide M have been found to be effective in treating platelet activating factor acether (PAF Acether)-induced maladies. Ginkgolide B has been found to be the most effective in this utility, as reported by Braquet in U.S. Pat. No. 4,734,280.

The term "ginkgolide" or "ginkgolides" herein includes the various ginkgolides disclosed in the book entitled "GINKGOLIDES, Chemistry, Biology, Pharmacology and Clinical Perspectives", J.R. Prous Science Publishers, Edited by P. Braquet (1988) as well as non-toxic pharmaceutically active derivatives thereof including, for example, tetrahydro ginkgolide derivatives, acetyl ginkgolide derivatives and alkyl esters of ginkgolides such as the monoacetate ginkgolide derivatives and tri-acetate ginkgolide derivatives as described in Okabe et al, "Ginkgolides", *J. Chem. Soc.* (C), pp. 2201–2206 (1967). The term "ginkgolide" herein also includes pharmaceutically acceptable salts of ginkgolides such as the sodium salts thereof.

In practical use, the ginkgolides are mixed with a non-toxic pharmaceutically acceptable carrier to form an injectable solution, for example, a physiological saline solution containing the ginkgolide or ginkgolide mixture.

The ginkgolides may be added to organ preservation solutions in which the organ to be transplanted is stored to allow the ginkgolide to permeate the organ, living tissue or living cells to be transplanted. Various commercially available organ preservation solutions may be utilized in accordance with the present invention including, but not limited to, Collins solution, Wisconsin solution, Belzer solution, Eurocollins solution, and lactated Ringer's solution.

An organ preservation solution will usually possess one or more of the following properties:

(1) The solution should have an osmotic pressure which is approximately equal to the inside of a mammalian cell. The solution is usually "hyperosmolar" which means that the solution has electrolytes such as $K^+$ and/or $Mg^{++}$ present in an amount sufficient to produce an osmotic pressure which is slightly higher than the inside of a mammalian cell.

(2) The solution should be capable of maintaining the ATP (adenosine triphosphate) level in the cells of the organ at approximately the usual level.

(3) The solution should allow optimum maintenance of glucose metabolism in the cells.

The organ preservation should contain an osmotic substance or a mixture of substances (e.g., electrolytes) which produce an osmotic pressure substantially the same as is present in a mammalian cell. An osmotic pressure (osmolality) of approximately 320 mOSm/l may be useful. These substances include: sugars such as dextrose, glucose, sucrose, lactose, and mannitol, with dextrose being preferred; proteins such as albumin, preferably serum albumin, more preferably human serum albumin; natural or synthetic colloids such as dextrans, polyvinyl pyrrolidine, pluronics, hydroxyethyl starch, Ficoll, gum arabic, polyethylene glycol and lipids; anions such as glucontate, $PO_r^{-2}$ and $Cl^-$; and cations such as $K^+$, $Na^+$ and $Mg^{+2}$. The anions and/or cations can be provided by water soluble compounds such as potassium dihydrogen phosphate ($KH_2PO_4$), sodium gluconate, magnesium gluconate, calcium salts (such as $CaCl_2$), NaCl, KCl and potassium bicarbonate.

The organ preservation solution may also contain optional ingredients including, but not limited to, an anticoagulant such as heparin; an antiinflammatory agent such as corticosteroid; growth hormones such as insulin; an energy source (e.g., glucose and fructose); a high-energy phosphate compound (e.g., ATP and creatine phosphate); a metabolite (e.g., coenzymes and amino acids); a material to remove toxic debris (activated charcoal and heavy metal chelators); a material to slow down tissue destruction (e.g., protease and peptidase inhibitors); a material to inactivate bacteria and viruses (e.g., antibiotics such as penicillin or antiviral agents such as methylene blue); a material to enhance survival in a cold environment (e.g, glycerol); a material to enhance survival during oxidative stress (e.g., glutathione and selenium, superoxide dismutase and carotene); a material to enhance wound healing (e.g., zinc oxide) and a pH indicator such as Phenol Red.

ATP may be added to the organ preservation solution. Alternatively, compounds which stimulate ATP synthesis such as adenosine, creatine phosphate or other compounds which supply $PO_4^{-2}$ may be added in an amount sufficient to stimulate ATP synthesis in an attempt to maintain the ATP level in the cells at approximately a normal level.

A preferred organ preservation solution is a sterile non-toxic solution which contains at least the following ingredients: (1) a substance or mixture of substances which produce an osmotic pressure substantially the same as the osmotic pressure in a mammalian cell, (2) potassium ions (K+) in a concentration of approximately 115 meq/l; and (3) a phosphate salt in an amount of approximately 85 meq/l. The substance or mixture of substances which produce an osmotic pressure substantially the same as the osmotic pressure inside a mammalian cell preferably includes a sugar such as dextrose in an amount of approximately 25 g/l.

Another preferred organ preservation solution comprises a ginkgolide or a mixture of ginkgolides in an amount of 50 to 600 mg/l; sugar in an amount of approximately 25 g/l; potassium ions in a concentration of approximately 115 meq/l; phosphate salt in a concentration of approximately 85 meq/l; an anticoagulant; and a buffer which maintains the pH of the solution at about 7.1 to 7.6.

The organ preservation solution is usually a basic solution having a pH of about 7.1 to 7.6, preferably about 7.3 to 7.5, more preferably about 7.4. The organ preservation solution may also contain a buffer such as $PO_4^{31\ 2}$, a bicarbonate compound such as sodium or potassium bicarbonate, and HEPES Buffer (Sigma Chemical Company) to maintain the pH at approximately the desired pH. During transplantation, the organ preservation solution is preferably kept at a temperature of 0° to 10° C., preferably 0° to 7° C., most preferably 5° to 7° C.

EXAMPLE 1

Materials and Methods

Twelve size and weight matched mongrel dogs underwent left single lung transplantation following ischemic periods of 20-24 hours. Donor dogs were anesthetized with sodium pentobarbital, 1 ml/kg body weight, intravenously and incubated. They were ventilated with 1% Halothane, 99% oxygen at a tidal volume of 15 ml/kg and a rate of 16 breaths/minute. A left thoracotomy was performed and the donor was heparinized with 5,000 units of heparin. Six dogs received 10 mg/kg Ginkgolide B in one liter of lactated ringers and six dogs received lactated ringers alone 30 minutes prior to harvest. The pericardium was opened and the left main pulmonary artery and left mainstem bronchus were dissected free. The bronchus was clamped distal to the tracheal bifurcation at end inspiration and the pulmonary artery was clamped just distal to the main pulmonary artery. The heart was arrested with an intraventricular injection of potassium (10 meq.). The lung was quickly removed by dividing the pulmonary artery distal to the clamp and creating an atrial cuff which included all of the pulmonary veins. The lung was placed in a pan of slush and the lung covered with slush. The pulmonary artery was cannulated with intravenous tubing and perfusion was begun with a modified Collins solution. The solution consisted of Travenol Electrolyte Solution for Kidney Preservation (Travenol Laboratories Inc., Deerfield, Ill. 60015) modified with dextrose (25 g/l) and heparin sodium (5,000 units/liter). Six dogs had 10 mg/kg of Ginkgolide B added to the preservation solution. The Travenol Electrolyte Solution for Kidney Preservation consists of the following electrolytes: 115 meq/l K+, 10 meq/l Na+, 85 meq/l $H_2PO_4$, 15 meq/l Cl−, 10 meq/l $HCO_3$. All lungs were perfused with 20 ml/kg at a pressure of 40 mmHg. An additional 5 ml/kg was given if the atrial effluent was not clear. The atrial cuff was clamped for ten seconds four times during the harvest to allow the pulmonary veins to distend and perfuse the entire pulmonary vascular tree. Lungs were then stored in 1 liter of preservation solution with the atrial cuff, pulmonary artery and bronchus clamped at 10° C. for 20 to 24 hours.

Recipient dogs were anesthetized and ventilated in an identical fashion to the donor. A left thoracotomy was performed and a left pneumonectomy was performed. Ginkgolide B (10 mg/kg) was infused in 1 liter of lactated Ringers solution 30 minutes prior to transplantation. The transplantation was performed after baseline and post pneumonectomy data were recorded. The atrial anastomosis was performed first using 4-0 prolene in a vertical mattress pattern. The arterial clamp was released and the pulmonary artery was allowed to backbleed while the pulmonary artery anastomosis was completed using 5-0 prolene suture. The bronchial anastomosis was completed using 4-0 prolene suture. The bronchial clamp was removed and the lung was perfused and ventilated for 30 minutes before post transplant data were recorded. The ischemic period was recorded from the time the donor bronchus was clamped and the heart arrested until the recipient bronchial and pulmonary artery clamps were removed. After 30 minutes of reperfusion the native pulmonary artery was ligated and post-ligation data were recorded.

Figure 2:
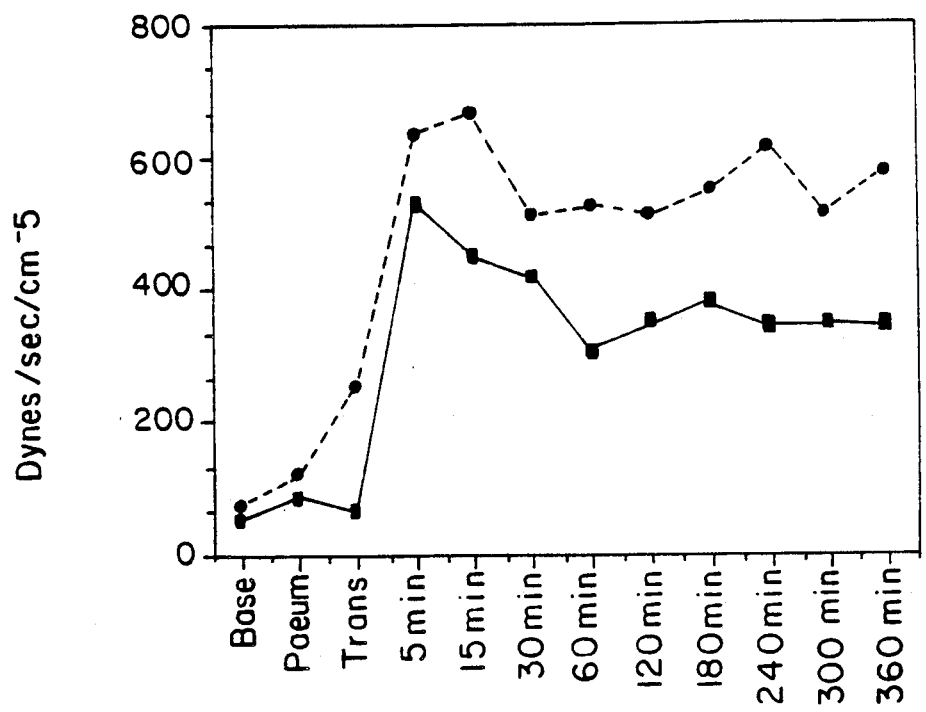
FIG. 2 is a graph showing the results of a pulmonary vascular resistance study described in Example 1 wherein the solid line represents the present invention and the dotted line represents a control.

Arterial blood gas analysis was performed on arterial blood gas analyzers. Blood pressure measurements were made with a Swann Ganz catheter and a femoral artery catheter connected to a pressure transducer. The results are shown in FIG. 1. Pulmonary vascular resistance was determined by the formula: mean pulmonary artery pressure—pulmonary capillary wedge pressure/cardiac output×80=pulmonary vascular resistance dyne/sec/cm-5. Lung compliance was determined by the formula: end inspiratory pressure—end expiratory pressure/tidal volume=compliance cm $H_2O$. Alveolar arterial oxygen difference was determined by the formula: atmospheric pressure-water pressure-$pO_2$-$pCO_2$. The results are shown in FIG. 2.

Results

Oxygenation was better in the Ginkgolide B group throughout the study. The mean $pO_2$ at the end of six hours was 243.5 vs. 71.7 mmHg for the control group ($p<0.02$), representing a decrease in $pO_2$ from baseline of 37.9% and 83.9%, respectively. The arterial-alveolar oxygen difference was less for the Ginkgolide B treated group, 431.8 vs. 606.0 ($p<0.02$). Pulmonary vascular resistance was less in the Ginkgolide B group after six hours, 346.9 vs. 663.67 dynes/sec./cm-5 ($p<0.007$). The decrease in compliance after six hours was 29.9% in the Ginkgolide B treated group vs. 49.9% for the controls, but this is not considered to be statistically significant ($p<0.09$).

Discussion

The findings of this study point out that reperfusion injury in a hypoxic preserved lung contributes significantly to post transplant dysfunction. Ginkgolide B improves post transplant pulmonary function, possibly by blocking the effects of platelet activating factor, and effectively extends the allowable period of hypoxic preservation. In accordance with the present invention it is theorized that ginkgolides may prevent leukocytes from releasing free oxygen radicals such as $O_2^-$ and $OH^-$ which injure endothelium in blood vessels of the transplanted organ.

What is claimed is:

1. A method for preventing or reducing reperfusion injury in living tissue or transplanted mammalian organs, which comprises:

contacting living tissue or an organ prior to reperfusion with an effective amount of a ginkgolide to reduce reperfusion injury in said tissue or organ, enhance blood oxygenation, and decrease vascular resistance.

2. The method of claim 1, wherein said organ is placed in an organ preservation solution containing said ginkgolide after the organ has been removed from a donor but prior to transplanting said organ in a recipient.

3. The method of claim 2, wherein said organ is stored in said organ preservation solution at a temperature of 0° to 7° C.

4. The method of claim 2, wherein said ginkgolide is present in said organ preservation solution at a concentration of 50 to 600 mg/liter.

5. The method of claim 1, wherein said ginkgolide is administered to a recipient of said organ at approximately the same time that said organ is transplanted into said recipient.

6. The method of claim 5, wherein ginkgolide is intravenously administered to said organ in an amount of 1 to 20 mg/kg of body weight of said recipient at a time between 1 to 30 minutes prior to reperfusion.

7. The method of claim wherein said ginkgolide is administered to the donor of said organ shortly said organ is removed from said donor.

8. The method of claim 6, wherein said ginkgolide is intravenously administered to said organ donor in an amount of 1 to 20 mg/kg of body weight of said donor at a time between 10 minutes to 12 hours prior to removal of said organ from said donor.

9. The method of claim 1, wherein said organ is a lung.

10. A method for preventing or reducing reperfusion injury in a transplanted mammalian organ, which comprises:

placing said organ prior to reperfusion in an organ preservation solution containing ginkgolide B at a concentration of 50 to 600 mg/liter, and which is at a temperature of 0° to 7° C., after said organ has been removed from a donor but prior to transplanting said organ in a recipient so as to reduce reperfusion injury in said organ, enhance blood oxygenation, and decrease vascular resistance.

11. A living tissue or living cell preservation solution comprising:

an effective amount of a ginkgolide to reduce reperfusion injury in living tissue or living cells which has been stored therein; and a substance or mixture of substances present in an amount sufficient to produce an osmotic pressure in said solution approximately equal to the osmotic pressure of mammalian cells.

12. The preservation solution of claim 11, wherein the substance is a sugar in an amount of approximately 25 g/l.

13. The preservation solution of claim 11, wherein the substance is dextrose in an amount of approximately 25 g/l.

14. The preservation solution of claim 11, wherein the substance is potassium ions in an amount of approximately 115 meq/l.

15. The preservation solution of claim 11, which comprises:

a ginkgolide or a mixture of ginkgolides in an amount of 50 to 600 mg/l;

sugar in an amount of approximately 25 g/l;

potassium ions in a concentration of approximately 115 meq/l;

phosphate salt in a concentration of approximately 85 meq/l;

an anticoagulant; and a buffer which maintains the pH of the solution at about 7.1 to 7.6.

* * * * *